(12) United States Patent
Beadle et al.

(10) Patent No.: US 7,345,212 B2
(45) Date of Patent: Mar. 18, 2008

(54) PROCESS FOR OLEFIN OLIGOMERIZATION

(75) Inventors: Stephen W. Beadle, Prairieville, LA (US); Georges M. K. Mathys, Bierbeek (BE); Cesar M. Cheng-Guajardo, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 197 days.

(21) Appl. No.: 10/509,165

(22) PCT Filed: Mar. 28, 2003

(86) PCT No.: PCT/US03/09516

§ 371 (c)(1),
(2), (4) Date: Sep. 27, 2004

(87) PCT Pub. No.: WO03/082778

PCT Pub. Date: Oct. 9, 2003

(65) Prior Publication Data

US 2005/0143616 A1     Jun. 30, 2005

Related U.S. Application Data

(60) Provisional application No. 60/368,864, filed on Mar. 29, 2002.

(51) Int. Cl.
*C07C 2/02* (2006.01)

(52) U.S. Cl. ............. 585/533; 585/520; 585/530; 585/532

(58) Field of Classification Search ........... 585/520, 585/530, 532, 533
See application file for complete search history.

(56) References Cited

U.S. PATENT DOCUMENTS

| 4,076,842 A | 2/1978 | Plank et al. ............ 423/328 |
| 4,855,527 A | 8/1989 | Page et al. ............ 585/527 |
| 4,870,038 A | 9/1989 | Page et al. ............ 502/62 |
| 5,026,933 A | 6/1991 | Blain et al. ............ 585/7 |
| 5,284,989 A | 2/1994 | Apelian et al. ......... 585/533 |
| 5,672,800 A | 9/1997 | Mathys et al. ......... 585/520 |
| 5,874,661 A | 2/1999 | Verrelst et al. ........ 585/671 |
| 6,013,851 A | 1/2000 | Verrelst et al. ........ 585/533 |
| 6,300,536 B1 | 10/2001 | Verrelst et al. ........ 585/533 |

FOREIGN PATENT DOCUMENTS

EP  0 311 310   5/1992

*Primary Examiner*—Glenn Caldarola
*Assistant Examiner*—In Suk Bullock
(74) *Attorney, Agent, or Firm*—Andrew B. Griffis

(57) ABSTRACT

A process for preparing a substantially linear olefinic hydrocarbon mixture is described in which a lower olefin feed comprising one or more $C_3$ to $C_6$ lower olefins is contacted in the presence of water and under olefin oligomerization conditions with a catalyst comprising surface-deactivated ZSM-23.

23 Claims, No Drawings

PROCESS FOR OLEFIN OLIGOMERIZATION

CROSS REFERENCE TO RELATED APPLICATIONS

This application is a National Stage Application of International Application No. PCT/US03/09516, filed Mar. 28, 2003, which claims the benefit of Provisional Application No. 60/368,864, filed Mar. 29, 2002. These applications are incorporated herein by reference.

FIELD

This invention relates to lower olefin oligomerization employing a molecular sieve to produce a higher olefin mixture, more specifically a substantially linear olefinic hydrocarbon mixture.

BACKGROUND

Olefinic hydrocarbons are employed as starting materials in the hydroformylation, or oxo, process, for the eventual manufacture of numerous valuable products, e.g., alcohols, esters and ethers derived therefrom, aldehydes, and acids. Additionally, olefinic hydrocarbons are employed as reactants in the alkylation of aromatic hydrocarbons, specifically for the manufacture of linear alkyl aromatics and linear alkylaryl sulfonates, for eventual formulation into surfactants used in a wide variety of applications. In many of these end uses, linear or lightly branched hydrocarbon chains have advantages compared with more heavily branched chains. In the oxo process, olefins with linear or lightly branched structures are more reactive than those with heavily branched chains and, for a given degree of branching, certain isomers are more reactive than others. In surfactants produced from alkylation of olefinic hydrocarbons and sulfonation of the alkyl aromatic product, highly branched materials exhibit very poor biodegradability. However, linear alkylaryl sulfonates often are not highly effective as cleaning agents. Use of surfactants produced from lightly branched olefin oligomers in detergent formulations is advantageous because such surfactants exhibit acceptable cleaning properties and yet are relatively biodegradable.

Processes for oligomerizing olefins to produce a hydrocarbon material with a reduced degree of branching are well known in the art, for example as described in U.S. Pat. Nos. 4,855,527; 4,870,038; 5,026,933; 5,284,989; 6,013,851; and 6,300,536.

U.S. Pat. No. 4,855,527 describes a process for producing high molecular weight essentially linear hydrocarbon oligomers from a lower olefin feedstock by employing a shape selective crystalline silicate catalyst (ZSM-23) which is surface deactivated.

U.S. Pat. No. 4,870,038 discloses a process for producing substantially linear hydrocarbons by oligomerizing propylene or butene by employing a surface inactivated, but internally active, ZSM-23 metallosilicate zeolite catalyst.

U.S. Pat. No. 5,026,933 teaches a process for producing substantially linear hydrocarbons by oligomerizing a $C_2$-$C_8$ olefin with siliceous acidic ZSM-23 zeolite having Brönsted acid activity; wherein the zeolite has acidic pore activity and wherein the zeolite surface is rendered substantially inactive for acidic reactions.

U.S. Pat. No. 5,284,989 is directed to a process for producing substantially linear hydrocarbons by oligomerizing a lower olefin with acidic aluminosilicate ZSM-23 zeolite having Brönsted acid activity; wherein the zeolite has acidic pore activity and wherein the zeolite surface is surface-deactivated for acidic reactions by contacting with oxalic acid.

U.S. Pat. No. 5,874,661 teaches that contacting a branched olefinic hydrocarbon material with a catalyst in the form of a molecular sieve having a 10-membered ring pore structure reduces the degree of branching of the material.

U.S. Pat. Nos. 6,013,851 and 6,300,536 provide a process for the oligomerization of an olefin feed with a molecular sieve catalyst, in which a zeolite surface layer is deposited on each particle of the molecular sieve, the zeolite containing silicon and at least one other selected element, the zeolite of the surface layer being of the same crystalline structure as the core and having a higher silicon:selected element ratio than that of the core. The resulting product is an olefin oligomer hydrocarbon material having a reduced degree of branching.

Hydration of an olefin feedstock in a conventional oligomerization process has been recognized in the art. U.S. Pat. No. 5,672,800 discloses that by using a hydrated alkene-containing feedstock in an alkene oligomerization process, the yields of higher molecular weight alkenes can be increased, and the catalyst becomes deactivated more slowly. U.S. Pat. No. 6,013,851, discussed previously, also describes hydration of an oligomerization feed.

It would be desirable to prolong the life of the catalyst and to control the degree of branching in an oligomerization process to produce a substantially linear olefin hydrocarbon product useful in a wide variety of end use applications.

SUMMARY

The present invention is directed to a process for preparing a substantially linear olefinic hydrocarbon mixture comprising contacting a feed comprising one or more $C_3$ to $C_6$ lower olefins in the presence of water and under olefin oligomerization conditions with a catalyst comprising surface-deactivated ZSM-23.

In one embodiment, the ZSM-23 is surface deactivated with a sterically hindered nitrogenous base, such as 2,4,6-collidine.

Typically, the concentration of water in the feedstock is in the range of from about 25 ppm to about 1000 ppm; such as from about 100 ppm to about 750 ppm, for example about 575 ppm to about 625 ppm. In particular, the feedstock may be water saturated.

Conveniently, the feedstock comprises a mixture of olefins selected from propylene, butene and mixtures thereof, and in one embodiment the mole ratio of propylene to butene in the feedstock is in the range of about 99:1 to about 1:99.

Conveniently, the water and feed are contacted at a temperature in the range of from about 20° C. to about 60° C.

Conveniently, the substantially linear olefinic hydrocarbon produced from the oligimerization process is a olefinic hydrocarbon mixture comprising at least 5 wt %, such as at least 20 wt %, for example at least 85 wt %, of mono-olefin oligomers of the empirical formula:

$$C_nH_{2n}$$

where n is greater than or equal to 6, said mono-olefin oligomers comprising at least 20 percent by weight of olefins having at least 12 carbon atoms, said olefins having at least 12 carbon atoms having an average of from 0.8 to 2.0 $C_1$-$C_3$ alkyl branches per carbon chain.

DETAILED DESCRIPTION OF THE EMBODIMENTS

The present invention provides a process for preparing a substantially linear olefinic hydrocarbon mixture by contacting a lower olefin feed in the presence of water and under olefin oligomerization conditions with a catalyst comprising surface-deactivated ZSM-23. The effect of the water addition is a decreased catalyst deactivation rate due to improved heat dissipation, resulting in prolonging the useful life of the catalyst, and a reduction in the degree of branching of the higher olefins produced as a product of the oligomerization process.

Catalyst

The oligomerization catalyst used in the process of the invention comprises ZSM-23 which has been surface deactivated, conveniently by treatment with a sterically hindered nitrogenous base.

ZSM-23 and its characteristic X-ray diffraction pattern are described in detail in U.S. Pat. No. 4,076,842, the entire contents of which are incorporated herein by reference. ZSM-23 is a molecular sieve having a pore size of 4.5×5.2 Angstroms, such as to freely sorb normal hexane but to provide constrained access to larger molecules. Typically, the ZSM-23 employed is an aluminosilicate having a silica-to-alumina molar ratio of at least 12 and acid cracking activity (alpha value) of about 10 to 300. In one embodiment, the ZSM-23 employed has an alpha value of about 25 and a crystal size of less than 0.1 micron and is conveniently composited with a binder, such as alumina. The catalyst may be in the form of cylindrical extrudates of about 1 to 5 mm in diameter.

Surface deactivation of the ZSM-23 employed in the present process is conveniently achieved by treatment with a sterically hindered nitrogenous base, whereby surface acid sites are neutralized without significant reduction in the internal acid activity of the zeolite. The degree of steric hindrance of the basic nitrogen compound should be sufficient to prevent entry of the compound into the internal pores of the catalyst, that is compound should have a minimum cross-sectional diameter greater than the effective pore size of the zeolite to be treated; i.e., greater than 5 Angstroms. However, excessive steric hindrance may prevent effective or complete interaction between the surface acid sites of the molecular sieve and the selected basic species. Examples of suitable sterically hindered nitrogenous base are organonitrogen compounds such as trialkyl pyridine compounds, and in particular 2,4,6-collidine (2,4, 6-trimethyl pyridine, gamma-collidine).

A process for surface deactivating a ZSM-23 catalyst with 2,4,6-collidine is described in U.S. Pat. No. 5,026,933, the entire contents of which are incorporated herein by reference.

Feedstock

The alkenes that can be oligomerized by the process of the invention are ethene, propene, and linear or branched $C_4$ to $C_{12}$-alkenes. The alkenes are preferably $C_3$ to $C_6$-alkenes. The process is particularly advantageous for the oligomerization of propene and butenes and may be used for the oligomerization of a single alkene, or of mixtures of alkenes of the same or of different carbon numbers. The alkene may if desired be diluted with another suitable gas, for example, a low molecular weight saturated hydrocarbon.

In one embodiment, the feedstock comprises a mixture of propylene and butene, in which the mole ratio of propylene to butene is in the range of about 99:1 to about 1:99, such as in the range of about 49:51 to about 5:95, for example in the range of about 35:65 to about 10:90.

Hydration

It has been discovered that when water is added to the above feedstock and/or to the reactor used in the oligomerization process, the life of the surface deactivated ZSM-23 catalyst is extended, as compared to that of an identical catalyst to which no water has been added. Further, hydration of the feedstock results in a reduction of the degree of branching of the higher olefins produced.

The feedstock is advantageously hydrated prior to entering the oligomerization reactor. The desired proportion of water may be incorporated by saturating the feed at an appropriate temperature, e.g., from 20 to 60° C., or by injecting water through a pump. For example, the feedstock may be passed through a thermostatted water saturator. Since the amount of water required to saturate the alkene feedstock will depend upon the temperature of the feedstock, control of the water concentration is effected by appropriate control of the temperature of the feedstock. In one embodiment, the concentration of water in the feedstock is in the range of from about 25 ppm to about 1000 ppm; such as in the range of from about 100 ppm to about 750 ppm, for example in the range of from about 575 ppm to about 625 ppm.

Process

Suitable oligomerization conditions include a temperature of about 160° C. to about 250° C., for example in the range of about 190° C. to about 230° C., such as in the range of about 210° C. to about 220° C.; a pressure in the range of about 500 psig (3447 kPa (gauge)) to about 1500 psig (10342 kPa (gauge)), for example in the range of about 750 psig (5171 kPa (gauge)) to about 1250 psig (8618 kPa (gauge)), and a feed weight hour space velocity (WHSV) in the range of about 0.1 $hr^{-1}$ to about 4.0 $hr^{-1}$, for example in the range of about 0.2 $hr^{-1}$ to about 3.0 $hr^{-1}$, and such as in the range of about 1.75 $hr^{-1}$ to about 2.25 $hr^{-1}$.

Where surface deactivation is achieved by treatment with a trialkyl pyridine compound, the feed to the oligomerization process may include additional trialkyl pyridine compound so that the surface properties of the zeolite are maintained during the process. For example, the feed conveniently contains about 1 ppm to about 25 ppm of 2,4,6-collidine. See for example the processes described in U.S. Pat. No. 5,026,933 and U.S. Pat. No. 4,870,038, the entire contents of each of which are fully incorporated herein.

Product

Lightly branched oligomers, referred to alternatively as substantially linear olefins or near linear olefins, are produced by the oligomerization process of the invention. Desired oligomerization products include $C_{10}+$ substantially linear olefin hydrocarbons. The catalytic path for feed comprising propylene, butene, and mixtures thereof provides a long chain which may have one or more lower alkyl (e.g., $C_1$-$C_3$ alkyl) substituents along the straight chain.

The substantially linear olefinic hydrocarbon produced by the present process is a olefinic hydrocarbon mixture comprising at least at least 5 wt %, such as at least 20 wt %, for example at least 85 wt %, of mono-olefin oligomers of the empirical formula:

$$C_nH_{2n}$$

where n is greater than or equal to 6, said mono-olefin oligomers comprising at least 20 percent by weight of olefins having at least 12 carbon atoms, said olefins having at least 12 carbon atoms having an average of from 0.8 to 2.0, such as about 0.8 to about 1.3, $C_1$-$C_3$ alkyl branches per carbon chain, measured by nuclear magnetic resonance spectroscopy ($^{13}C$ NMR).

In one embodiment, the average degree of branching of the $C_8$ fraction is in the range of from about 0.90 to about 1.30, such as in the range from about 0.95 to about 1.20, for example in the range of about 0.95 to about 1.05; the average degree of branching of the $C_{12}$ fraction is in the range of from about 1.05 to about 1.60, such as in the range from about 1.05 to about 1.50, for example in the range of about 1.05 to about 1.40; and the average degree of branching of the $C_{16}$ fraction is in the range of from about 1.10 to about 1.70, such as in the range from about 1.20 to about 1.60.

The invention will now be more particularly described with reference to the following prophetic examples.

EXAMPLE 1

A feedstream having the hydrocarbon composition given in Table 1 and comprising from about 50 wt. % to about 70 wt. % butenes and from about 0 wt. % to about 10 wt. % propylene and containing from about 1 ppm to about 25 ppm of 2,4,6-collidine is passed through a thermostatted water saturator. The temperature of the feedstock is from about 30° C. to about 50° C. and the water concentration of the feedstock is from about 575 ppm to about 625 ppm. A ZSM-23 catalyst which has been treated with 2,4,6-collidine in the manner described in U.S. Pat. No. 5,026,933 is then used to oligomerize the feed at a temperature of from about 200° C. to about 225° C., a pressure of about 1100 psig (7584 KPa (gauge)) to about 1400 psig (9653 KPa (gauge)) and a WHSV of from about 1.75 hr$^{-1}$ to about 2.25 hr$^{-1}$. The product of the oligomerization process is composed of from about 40 wt % to about 50 wt % of $C_8$ olefins, from about 30 wt % to about 40 wt % of $C_{12}$ olefins and from about 5 wt % to about 15 wt % of $C_{16}$ olefins. The average degree of $C_1$-$C_3$ alkyl branching of the $C_8$, $C_{12}$ and $C_{16}$ fractions is determined by $^{13}C$ NMR and is found to be from about 0.95 to about 1.05, from about 1.05 to about 1.40, and from about 1.20 to about 1.60, respectively. It is believed that, based on the condition and reactivity of the catalyst, addition of water to the feed extends the useful life of a catalyst subjected to prolonged practice of the process as compared to the useful life of a catalyst with an unhydrated feed subjected to such use.

TABLE 1

| Component | From About (Wt. %) | To About (Wt. %) |
| --- | --- | --- |
| Ethane | 0.03 | 0.09 |
| Propane | 0.86 | 0.91 |
| Propylene | 0.14 | 0.17 |
| Isobutane | 23.89 | 27.46 |
| n-Butane | 16.20 | 22.73 |
| Butene-1 | 20.07 | 23.88 |
| Isobutylene | 0.78 | 1.07 |
| t-Butene-2 | 17.96 | 19.98 |
| c-Butene-2 | 11.71 | 12.73 |
| Butadiene-1,3 | 0.00 | 0.09 |
| Isopentane | 0.53 | 1.17 |
| Pentene-1 | 0.00 | 0.08 |
| Dimethyl Ether | 0.07 | 0.15 |
| MTBE | 0.00 | 0.01 |
| TAME | 0.00 | 0.01 |
| Total Butenes | 50.81 | 57.30 |
| Total Pentenes | 0.00 | 0.08 |

EXAMPLE 2 (COMPARATIVE)

The feedstream in Example 2 is identical to that described in Example 1 except that the feed is not passed through a water saturator. The feedstream is subjected to the same oligomerization process as set forth in Example 1. The temperature of the feedstock is from about 30° C. to about 50° C. and the water concentration of the feedstock is from about zero ppm to about 5 ppm. The product of the oligomerization process contains from about 10 wt % to about 50 wt % of $C_8$ olefins, from about 30 wt % to about 40 wt % of $C_{12}$ olefins and from about 5 wt % to about 25 wt % of $C_{16}$ olefins. The average degree of methyl branching of the $C_8$, $C_{12}$ and $C_{16}$ fractions is determined by $^{13}C$ NMR and is found to be from about 0.95 to about 1.05, from about 1.05 to about 1.40, and from about 1.20 to about 1.60, respectively.

Results indicate that the active catalyst life after completion of the process set forth in Example 1 exceeds the active catalyst life remaining after completion of the process set forth in Example 2.

While the present invention has been described and illustrated by reference to particular embodiments, those of ordinary skill in the art will appreciate that the invention lends itself to variations not necessarily illustrated herein. For example, it is contemplated that an olefin feed is contacted with water vapor. It is also contemplated that liquid water or water vapor is separately added to the reactor, injected into the feedstream or added to the catalyst. For this reason, then, reference should be made solely to the appended claims for purposes of determining the true scope of the present invention.

The invention claimed is:

1. A process for preparing a substantially linear olefinic hydrocarbon mixture comprising the step of contacting a lower olefin feed comprising one or more $C_3$ to $C_6$ lower olefins in the presence of water and under olefin oligomerization conditions with a catalyst comprising surface-deactivated ZSM-23, said substantially linear olefinic hydrocarbon mixture characterized by having at least two of methyl, ethyl, and propyl branches as measured by $^{13}C$ NMR.

2. The process according to claim 1, wherein said ZSM-23 has been surface deactivated with a sterically hindered nitrogenous base.

3. The process according to claim 2, wherein the nitrogenous base is 2,4,6-collidine.

4. The process according to claim 1, wherein the feed comprises propylene and butene.

5. The process according to claim 4, wherein that the mole ratio of propylene to butene in the feed is in a range of about 99:1 to about 1:99.

6. The process according to claim 4, wherein the mole ratio of propylene to butene in the feed is in a range of about 49:51 to about 5:95.

7. The process according to claim 4, wherein the mole ratio of propylene to butene in the feed is in a range of about 35:65 to about 10:90.

8. The process according to claim 1, wherein the concentration of water in the feed is in a range of from about 25 ppm to about 1000 ppm.

9. The process according to claim 1, wherein the concentration of water in the feed is in the range of from about 100 ppm to about 750 ppm.

10. The process according to claim 1, wherein the concentration of water in the feed is in the range of from about 575 ppm to about 625 ppm.

11. The process according to claim 1, wherein the water is contacted with the feed prior to contacting of the feed with the catalyst.

12. The process according to claim 11, wherein the water and the feed are contacted at a temperature in the range of from about 20° C. to about 60° C.

13. The process according to claim 1, wherein the feed is water-saturated.

14. The process according to claim 1, wherein the oligomerization conditions comprise a pressure in the range of from about 500 psig (3447 KPa (gauge)) to about 1500 psig (10342 KPa (gauge)).

15. The process according to claim 1, wherein the oligomerization conditions comprise a pressure in the range of from about 750 psig (5171 KPa (gauge)) to about 1250 psig (8618 KPa (gauge)).

16. The process according to claim 1, wherein the oligomerization conditions compose a temperature in the range of from about 160° C. to about 250° C.

17. The process according to claim 1, wherein the oligomerization conditions compose a temperature in the range of from about 190° C. to about 230° C.

18. The process according to claim 1, wherein the oligomerization conditions comprise a temperature in the range of from about 210° C. to about 220° C.

19. The process according to claim 1, wherein the oligomerization conditions comprise a weight hourly space velocity of from about 0.1 hr$^{-1}$ to about 4.0 hr$^{-1}$.

20. The process according to claim 1, wherein the oligomerization conditions comprise a weight hourly space velocity of from about 0.2 hr$^{-1}$ to about 3.0 hr$^{-1}$.

21. The process according to claim 1, wherein the oligomerization conditions comprise a weight hourly space velocity of from about 1.75 hr$^{-1}$ to about 2.25 hr$^{-1}$.

22. The process according to claim 1, wherein the substantially linear olefinic hydrocarbon mixture comprises at least 85% by weight of mono-olefin oligomers of the empirical formula:

$$C_nH_{2n}$$

where n is greater than or equal to 6, said mono-olefin oligomers comprising at least 20 percent by weight of olefins having at least 12 carbon atoms, said olefins having at least 12 carbon atoms having an average of from 0.8 to 2.0 $C_1$-$C_3$ alkyl branches per carbon chain.

23. The process according to claim 22 wherein said olefins having at least 12 carbon atoms have an average of from 0.8 to 1.3 $C_1$-$C_3$ alkyl branches per carbon chain.

* * * * *